United States Patent

Demello et al.

[11] Patent Number: 5,846,830
[45] Date of Patent: Dec. 8, 1998

[54] DETECTING FECAL AND/OR URINARY CONTAMINATION IN MEATS AND POULTRY

[76] Inventors: Frank J. Demello, 6134 Woody La. SE., Fridley, Minn. 55432; Ophelia Drake, 103 Merrill Ave., Fremont, Calif. 94539

[21] Appl. No.: 884,511

[22] Filed: Jun. 27, 1997

[51] Int. Cl.[6] ........................... G01N 21/64; G01N 33/12
[52] U.S. Cl. ...................... 436/21; 436/172; 250/459.1; 250/910
[58] Field of Search ............................ 436/21, 164, 172; 452/198; 250/459.1, 461.2, 910

[56] References Cited

U.S. PATENT DOCUMENTS 5,621,215  4/1997  Waldroup et al. .................... 250/461.2

FOREIGN PATENT DOCUMENTS 6271899  9/1994  Japan .

OTHER PUBLICATIONS

The Merck Index, Tenth Edition (1983), p. 595.

*Primary Examiner*—Jeffrey Snay
*Attorney, Agent, or Firm*—Christopher John Rudy

[57] ABSTRACT

Fecal and/or urinary contamination in meat and poultry can be detected by internalizing into a suitable livestock system a material containing a marker substance, and detecting for the presence or absence of the marker substance on meat values. Typically, the detection is carried out upon slaughter of the livestock and preparation of its meat values for consumption. As an illustration, a flour substance may be included in livestock feed, and, in turn, its presence or absence detected on the meat values under appropriate light conditions as an indicator of fecal contamination. For example, the flour substance may be flourescein, the presence or absence of which may be detected on the processed meat or poultry by ultraviolet light. A detection kiosk may be employed to assist in the detection.

10 Claims, 1 Drawing Sheet

U.S. Patent   Dec. 8, 1998   5,846,830
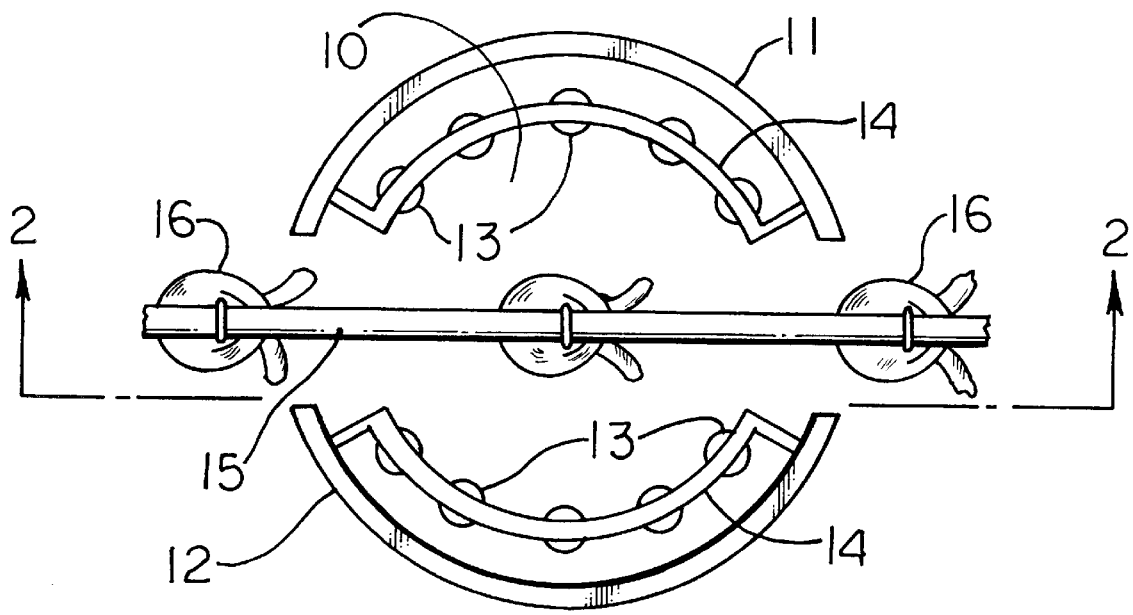
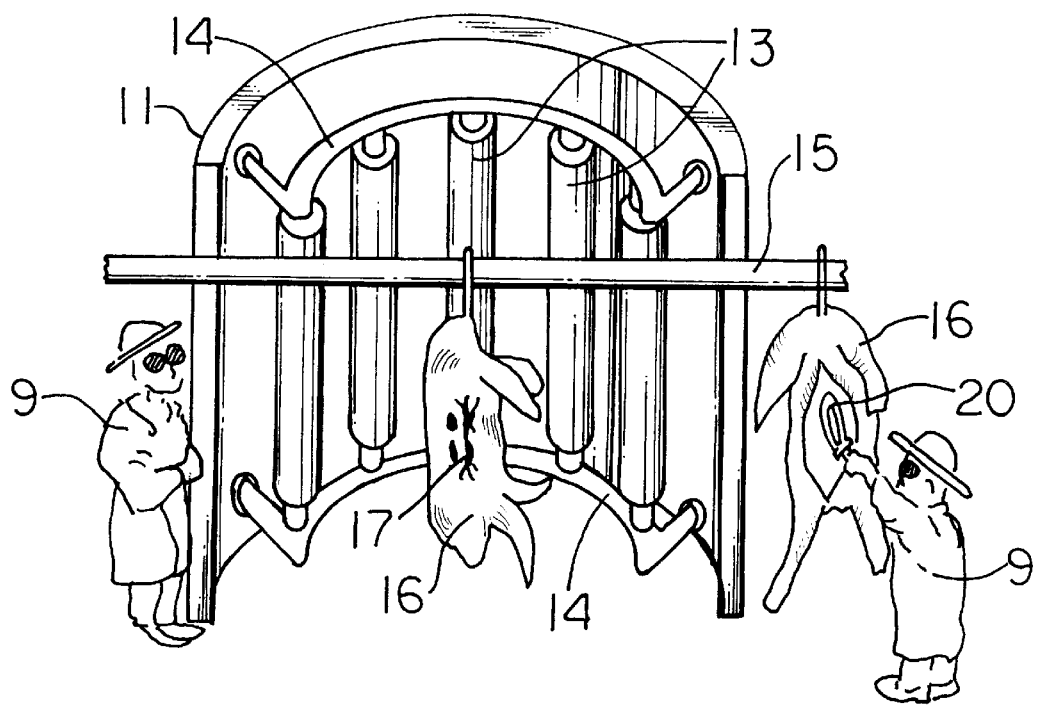

5,846,830

DETECTING FECAL AND/OR URINARY CONTAMINATION IN MEATS AND POULTRY

FIELD

The present invention concerns an apparatus and a method for the detection of fecal and/or urinary contamination in meats and poultry, etc. In particular, it concerns detection of such by employing a marker substance suitably internalized by livestock, which can appear and be detected on the meat, poultry or other variety of flesh with any such contamination, for instance, after slaughter of the livestock.

BACKGROUND

The meat industry has been implicated in serious cases of food poisoning. The Center for Disease Control in Atlanta, Ga. has estimated that in the United States some nine thousand people die each year from food related illnesses. A number of problems have been reported, often after individuals ate undercooked hamburger at restaurants. More cases may go unreported where the problem is not severe, or the individual simply attributes his malaise to something he ate which did not agree with him. In general, the source of these infections are ubiquitous agents such as bacteria and/or their toxins, which are carried on the hides, feathers, and in the intestinal tract of domestic animals, and which contaminate the meat intended for human consumption. For example, an *E. coli* strain has been implicated as the culprit in the above meat contamination.

Serious flaws exist in the manner in which meat is inspected in slaughter houses. The National Academy of Sciences has stated that the current method of meat inspection, in use in the U.S. since 1906, is inadequate in protecting the public from meat related diseases. In the U.S. in general, government agents such as of the Food and Drug Administration examine the slaughtered carcasses visually for signs of abnormalities, tumors or gross fecal contamination, without touching the meat, and they smell the carcasses for obvious putrid odors. Bacterial contamination, which does not exhibit these obvious markers, goes unnoticed.

However, it is bacterial microorganisms, which are the cause of much infection in meats. Such microorganisms are most commonly spawned in the digestive tracts of the animals, and thrive in feces. These contaminating microorganisms can multiply and secrete toxic compounds even in cold storage. To detect and identify these microorganisms generally requires elaborate and time-consuming bacteriological procedures. The meat must be held in storage until the results of the laboratory analyses verifying its safety is reported. This could be costly to the producer.

Poultry presents another serious contamination: salmonella. For example, the U.S. Department of Agriculture in 1992 estimated that forty-nine percent of all the poultry processed in the U.S. is contaminated with salmonella and still passed inspection. This infection is in a constant state of recycle in the chicken industry because breeders feed livestock chicken waste chicken parts contaminated with the organism. Also, healthy chicken, even those which are raised under ideal farm conditions, become contaminated after slaughtering when they are chilled in the same cooling vats with contaminated chicken.

Furthermore, the routine use of growth promoting antibiotics in the feed of livestock increases the chance of producing resistant organisms which can enter the food chain.

Granted, the meat and poultry industry, in particular as represented by the volume producers, has taken large strides in modernizing its processing plants and improving its technology. However, the emphasis has been on mechanization and speed, and sanitation and infection control lagged.

Accordingly, the meat and poultry industry is in dire need of a fast and efficient procedure to detect contamination in meats.

SUMMARY

The present invention provides a method for detecting fecal and/or urinary contamination in meat and poultry, which method comprises suitable internalization into a livestock system of a material containing a marker substance, and detecting for the presence or absence of the marker substance on meat values as an indicator of such contamination. Typically, the detection is carried out upon slaughter of the livestock and preparation of its meat values for consumption. Apparatus for carrying out the method such as in a detection kiosk is also provided.

The invention is useful in meat and poultry inspection. Significantly, simple, easy, fast, efficient, non-invasive and practical detection of contamination in meat and poultry caused by feces, urine and/or feces or urine borne agents is provided. As an illustrative exemplification of this, it has been discovered that—by mixing small amounts of fluorescein dye with the food and/or water of the animals, say, six to ten hours before slaughtering; allowing the marked feed or water to be ingested by the animals; slaughtering the animals, and then exposing the carcasses to ultraviolet (UV) light—fecal contamination fluoresces under the UV light. Generally at a slightly higher level of the dye, fluorescence may be detected with respect to urine. The present invention can be practiced conveniently at the site of meat processing, or even at the point of consumer sale.

Numerous further advantages attend the invention.

DRAWINGS

The drawings form part of the specification hereof. In the drawings, the following is briefly noted:

FIG. 1 is a top plan view including a detection kiosk of the invention, in which the method of the invention can be practiced.

FIG. 2 is a view of the embodiment of FIG. 1 taken along 2—2.

ILLUSTRATIVE DETAIL

The invention can be further understood by reference to the following detail, which may be taken in conjunction with the drawings. The same is to be taken in an illustrative and not necessarily limiting sense.

Fecal and/or urinary contamination in meat and poultry can be detected by the practice of the present invention. The main source of contamination of meat and poultry is from the feces and urine of the livestock, and thus, the invention is most opportune.

In general, in the practice of the present invention, and in particular as would accompany the practice of the method embodied therein, a material containing a marker substance is suitably internalized into a livestock system. In turn, the presence or absence of the marker substance on meat values as an indicator of such contamination is detected.

Livestock include herein mammalian livestock including bison, camels, cattle, deer, goats, horses, llamas, oxen, pigs, rabbits, sheep, squirrels, and so forth and the like, whose edible flesh and organs are generally termed "meat," and avian livestock including chicken, duck, emu, geese, ostrich, pheasant, ruffed grouse, turkey, and so forth and the like, whose edible flesh and organs are termed "poultry." of course, as dictated by the surrounding context, the term "meat" can include herein the mammalian meat and poultry, plus other meats to include edible portions of fish, frogs, snakes, turtles, worms, and so forth and the like. Thus, livestock can include any suitable flesh bearing animal. The edible flesh can be especially considered to be that from muscle tissue, with or without bone. "Meat values" refers to portions of the livestock accompanied by or of meat.

The material containing a marker substance can include the marker substance in combination with a feeding and/or watering material. Alternatively, the marker substance may be provided by itself for internalization by the livestock. Internalization into the system of the livestock by force feeding, injection, suppository, and so forth and the like may be employed, and accordingly, the material for employment as a carrier for the marker substance can include suitable aqueous solutions; gaseous, liquid or solid medicines; other gasses, liquids or solids, and so forth and the like. However, ingestion is preferred.

Preferably thus, livestock are fed or watered with a material containing the marker substance. The marker substance, thus internalized by ingestion, passes into the digestive system of the livestock, and then the presence or absence of the marker substance on the meat values is suitably detected.

Feeding material can include any conventional feed including bark; grains including corn, flax, oats, rye, wheat, and so forth and the like; hay crops such as alfalfa, clover, timothy, range grass, and so forth and the like; legumes including beans, peas, and so forth and the like; nuts; processed foods such as pellets, sweetened pellets, and so forth and the like; natural range cover; silage, and so forth and the like. Other materials such as salt blocks, mineral blocks, soil, sawdust, vitamin blocks, and so forth and the like may be employed as a feeding material or mixed with the feed. Watering material can include any liquid which the livestock is likely to drink including water, juices, milk, saps, and so forth and the like. With respect to the material for employment as a carrier, the marker substance may be communited, ground with, admixed with, poured on, processed with, sprayed on, stirred in, and so forth and the like, so as to mix the same.

The marker substance may be any substance that would enhance the detection of fecal and/or urinary contamination in meats or poultry. For instance, bright compositions, compounds or dyes; luminescent compositions, compounds or dyes; magnetic substances; malodorous substances, for example, which may be detected only by trained dogs; radioactive substances, and so forth and the like may be employed. Desirably, the marker substance is disguised, i.e., by humans, it is not readily detectable on the meat values under the usual or normal conditions of air quality, light, temperature, and so forth, but it is detectable as by another species or under activation conditions. For example, luminescent dyes may be employed as a disguised marker substance, flours and phosphors among them, which are undetectable by the naked eye under the usual conditions but which are detectable under or from stimulation by light of a certain intensity and/or wavelength such as of impingement of suitable high intensity, monochromatic light from the visible spectrum, or impingement of suitable infrared, radio, ultraviolet or X-ray radiation. In particular, non-cyanide fluorescent/phosphorescent dye(s) which also conform to such standards as the lead-content standards of ASTM D-4236 are preferred. An exemplary fluorescent dye, which can be activated by UV light, is fluorescein, also known as resorcinolphthalein or 3',6'-dihydroxyspiro(isobenzofuran-1 (3H),9'-{9H}xanthen)-3-one, etc., or suitable salts thereof to include its disodium salt, uranine yellow, also known as soluble fluorescein, D & E yellow No. 8, etc., and its potassium salt. Although the fluorescein dye is preferred because it stays predominately in the intestinal tract after feeding to the animals for slaughter and is not absorbed to a great extent by the blood stream, especially when fed a lower levels, feeding increased levels of the dye can leave its traces in the bladder, etc.

Any suitable amount of the marker substance may be employed in the practice of the invention. For example, the dose of one gram (g) of fluorescin,dye per kilogram (kg) of feed has been found to be more than adequate to detect fluorescence.

The detection of the marker substance, which has passed into the system of the animal can be done at any suitable time, while the animal is alive, for example, if preliminary indication of cleanliness is desired. Typically, however, the detection is carried out upon slaughter of the livestock and preparation of its meat values for consumption or sale.

With particular reference to the drawings of FIGS. 1 & 2, an inspector 9, who wears protective clothing and glasses, can be seen working in the chamber of multi-part kiosk 10 at a slaughterhouse or butcher facility. The kiosk 10 has separate walls 11 & 12 on which can be mounted marker substance activator device(s), for example, UV light sources 13 energized by power lines 14. A carcass transport device, for example, overhead conveyor line 15, or a dolly, cart, and so forth and the like, brings carcasses 16 through the kiosk 10 while the lights 13 operate. The carcasses are from animals which had been fed a fluorescein dye some six to twelve hours or a day or so before slaughtering. Traces of the dye 17 fluoresce to indicate fecal. contamination on the outside of the carcass 13 while the carcass 13 is in the light kiosk 10. In addition (FIG. 2) another inspector 9, who also wears protective clothing and glasses and who is outside the kiosk 10, views the inside of the carcass 13, looking for fecal and/or urinary contamination as evidenced by the dye, with the assistance of a hand held UV light wand 20.

The invention may be provided in automated or semi-automated form. The detection chamber, which, for example, can be operated under UV light, can be enclosed so as to not expose an operator to extra irradiation. A monitor can be installed, which signals, for example, by buzzing, or be lighting or movement of a dial, when contamination is detected. A hand-held UV wand can be used to examine certain parts of the carcass which are suspect. many monitors are commercially available, which can detect miniscule amounts of fluorescence. However, those can be expensive and laborious to operate. Nevertheless, use of the same may be employed in the practice of the invention.

Store butchering or consumer sales locations can be equipped with suitable activation stations. For example, grocery store meat counters may be provided with a UV light source, under which meats from animals appropriately fed fluorescein type dye materials can be viewed for traces of possible contamination.

The following example further illustrates the invention. Therein, parts and percentages are by weight.

EXAMPLE

MATERIALS:

Livestock and Feeds:

Chicken: Young broilers weighing about five pounds.

The Feed: Supersweet feed was bought from a local supplier. It was made of corn, oats, soybeans, vitamins and minerals. The animals were housed in individual cages and given water ad lib. Straw was used for bedding. The cages were cleaned once per week.

Rabbit: Albino rabbits weighing about seven pounds.

The Feed: Rabbit pellets obtained from the local mill. It contained corn, soybean meal, oats, hay, vitamins and minerals. Animals were housed individually, in cages, on a bed of straw, and given water ad lib. The cages were cleaned once per week.

Mutton: Spring lambs weighing about one hundred pounds.

The Feed: Cracked corn and oats mixture, ninety percent corn and ten percent oats. Meadow hay and water were given ad lib. The animals were confined in individual pens on clean straw. The straw and water were replaced daily.

Fluorescent Dyes:

A) Crayola Washable Neon Poster Paint: Yellow, red and orange.

B) Kodak Fluorescent Poster Paint: Yellow, red and orange.

C) Fisher-Across Water-soluble Fluorescein Dye.

METHODS:

All the animals were fed their respective feed without the dye for a period of two weeks so that they got adjusted to the feed. Seventy-two chicken, seventy-two rabbits, and twelve lambs were used with each dye. Dye compositions A and B above were relatively difficult to mix with the feed because of their thick consistency. The lambs and rabbits ate around the dye of these mixtures and did not consume them, but the chicken, apparently attracted to the bright colors, ate the dye in spite of its lumpy consistency. The experimentation with these lumpy dye mixes was discontinued with the lamb and rabbit subjects but was continued with the chicken subjects.

The methods were repeated with dye composition C above. All the animals accepted and ate the feed with this dye without any hesitation. In one set of runs with this dye, the following was carried out:

Twenty-two chickens were used, as follows:
Two chickens were fed no dye in their feed (control).
Two chickens were fed 1 g of dye per kg of feed.
Two chickens were fed 4 g of dye per kg of feed.
Two chickens were fed 8 g of dye per kg of feed.
Two chickens were fed 16 g of dye per kg of feed.
Two chickens were fed 32 g of dye per kg of feed.
Two chickens were fed 64 g of dye per kg of feed.
Two chickens were fed 128 g of dye per kg of feed.
Two chickens were fed 256 g of dye per kg of feed.
Two chickens were fed 512 g of dye per kg of feed.

Twenty-two rabbits were used, as above for the chickens.

Twelve lambs were used, as follows:
Two lambs were fed no dye in their feed (control).
Two lambs were fed 1 gram (g) of dye per kilogram (kg) of feed.
Two lambs were fed 10 g of dye per kg of feed.
Two lambs were fed 100 g of dye per kg of feed.
Two lambs were fed 200 g of dye per kg of feed.
Two lambs were fed 300 g of dye per kg of feed.

The animals were fed these diets for fourteen days. They were observed very closely for any physical signs of illness, and then sacrificed and autopsied. All the internal organs were examined for pathology visually and under a UV light.

RESULTS:

With respect to the chicken, the dye was visibly detected in its lowest concentration of 1 g per kg of feed. The fluorescence was readily apparent under activation of the UV light. It was concentrated in the food pouch, gizzard, and intestinal tract. It was also evident in any area of the flesh which was contaminated with feces. The heart and lungs had no fluorescence, as were the liver and spleen. There was a slight tinge of fluorescence in the bladder. At a feed concentration of 128 g of dye per kg of feed, the liver showed a blanching effect but no fluorescence under the UV light. Other fluorescence was very intense. At a feed concentration of 512 g of the dye per kg of feed, the effect of the dye was overwhelming. It stained the feathers of the bird, as well as its beak and feet. The liver and spleen were severely blanched—whitish in color—under ambient light but did not fluoresce under the UV light; the rest of the organs looked normal, and yet, these birds did not seem to suffer any noticeable ill effects while alive. The chickens were washed, plucked, gutted, cleaned, and then stored in a regular household refrigerator for seven days. Then they were frozen in a regular household freezer and examined again after four weeks. The entire flesh part, liver and heart of the chickens which had been given concentrations of up to 64 g of dye per kg of feed were cooked and consumed by the human family without observable ill effects, and this over a significantly long period of time. The rest of the chickens were cooked and fed to the farm dogs and cats. The dogs and cats were observed for side effects, and no side effects could be observed.

With respect to the rabbits, results similar to those of the chickens, above, were observed, except that blanching of the liver and spleen appeared first in animals which had eaten feeding mixtures with 256 g of dye per kg of feed. The dye also stained the mouth, whiskers, and fur of the rabbits. Stained flesh was evident after refrigeration and freezing. The dye was washed with quaternary ammonium compounds, simple detergents which are known to be safe to use with food products. Carcasses, livers and hearts of the rabbits which had been fed lower concentrations of the dye were cooked and consumed by the family; those with higher concentrations were fed, like the chickens, to the farm dogs and cats. No ill effects were observed.

With respect to the lambs, large concentrations of the dye were tolerated very well. The 300-g level of dye per kg of feed did not change the color or the consistency of the liver or the spleen. All the internal organs looked healthy. The only contamination which was observed occurred when the intestines were intentionally nicked to observe the effect of the dye under UV light as an indicator of fecal contamination. The lambs were cut up, wrapped, and frozen. The mutton, i.e., the entire lamb of carcass, liver and heart—except the head, legs and entrails, was consumed by the human family with no observable ill effects, and this over a significantly long period of time.

CONCLUSION

The present invention is thus provided. Numerous modifications can be effected within its spirit, the literal claim scope of which is particularly pointed out as follows:

We claim:

1. A method for detecting fecal and/or urinary contamination in meat or poultry, which method comprises suitable internalization into a livestock system of a material containing a marker substance, and detecting for the presence or absence of the marker substance on meat values as an indicator of such contamination wherein said marker substance includes fluorescein or a suitable salt thereof.

2. The method of claim 1, wherein the detection is carried out upon slaughter of the livestock and preparation of its meat values for consumption.

3. The method of claim 2, wherein said internalization is by ingestion.

4. The method of claim 1, wherein said detecting is done with a light source invisible to the naked eye.

5. The method of claim 1, wherein the meat values are of mammalian flesh.

6. The method of claim 1, wherein the meat values are of poultry.

7. A method for detecting fecal contamination in meat or poultry, which method comprises:

adding a material containing a marker substance to feed or water for livestock;

feeding or watering livestock with the feed or water having the added material containing the marker substance;

allowing the marker substance to pass into the digestive system of the livestock;

slaughtering the livestock, and then detecting for the presence or absence of the marker substance on meat values as an indicator of such contamination wherein said marker substance includes fluorescein or a suitable salt thereof, and said detecting is conducted in the presence of UV light.

8. The method of claim 7, wherein the meat values are of mammalian flesh.

9. The method of claim 7, wherein the meat values are of poultry.

10. The method of claim 1, wherein urinary contamination is detected with the assistance of ultraviolet light.

\* \* \* \* \*